United States Patent [19]

Groe

[11] Patent Number: 4,881,183

[45] Date of Patent: Nov. 14, 1989

[54] METHOD AND APPARATUS FOR EMISSION TESTING

[75] Inventor: David E. Groe, Oakwood Hills, Ill.

[73] Assignee: Sun Electric Corporation, Crystal Lake, Ill.

[21] Appl. No.: 173,419

[22] Filed: Mar. 25, 1988

[51] Int. Cl.$^4$ ............... G01N 21/00; G06F 15/20
[52] U.S. Cl. .................................. 364/550; 364/497; 364/571.04; 364/571.08
[58] Field of Search ............ 364/571.01, 571.02, 364/571.03, 571.04, 571.05, 571.06, 571.07, 571.08, 431.04, 550, 551.01, 497

[56] References Cited

U.S. PATENT DOCUMENTS

| | | | |
|---|---|---|---|
| 4,093,871 | 6/1978 | Plumb et al. | 364/571.03 |
| 4,159,523 | 6/1979 | Neer | 364/571.05 |
| 4,254,469 | 3/1981 | Whitely | 364/571.05 |
| 4,314,344 | 2/1982 | Johns et al. | 364/571.05 |
| 4,328,546 | 5/1982 | Kreft et al. | 364/431.04 |
| 4,348,732 | 9/1982 | Kreft | 364/571.08 |
| 4,357,668 | 11/1982 | Schwartz et al. | 364/497 |
| 4,390,956 | 6/1983 | Cornforth et al. | 364/571.03 |
| 4,454,852 | 6/1984 | Hasegawa | 364/431.04 |
| 4,454,853 | 6/1984 | Hasegawa | 364/431.04 |
| 4,467,435 | 8/1984 | Warnke et al. | 364/497 |
| 4,576,035 | 3/1986 | Hooven et al. | 364/571.03 |
| 4,638,443 | 1/1987 | Kaneyasu et al. | 364/497 |
| 4,672,566 | 6/1987 | Asano et al. | 364/571.04 |

*Primary Examiner*—Felix D. Gruber
*Attorney, Agent, or Firm*—Nicholas A. Camasto

[57] ABSTRACT

A computerized emissions tester determines concentrations of HC, CO, and CO2 in exhaust emissions. An IR test bench assembly develops an analog voltage representative of the concentration of a particular gas in a sample gas of known concentration. Data related to calibration pressure, voltage offset and voltage gain are stored in non-volatile memory EEPROM. Algorithms relating voltage and concentration of the particular gases are included in software. The pressure of an exhaust emission is compared with the calibration pressure data in memory and a correction is applied to the tester output. The data relating to the voltage offset and gain factor are also used to compensate the tester output.

2 Claims, 3 Drawing Sheets

FIG. 3

HC: $$\text{CONCENTRATION} = \frac{.0848662 + 165.45\,V}{1 - .0160776\,V - .000119486\,V^2}$$

CO: $$\text{CONCENTRATION} = \frac{-.0034791 + .146485\,V + .0514146\,V^2}{1 - .053123\,V\ \ .00188917\,V^2}$$

CO$_2$: $$\text{CONCENTRATION} = \frac{-.024569 + .87272\,V}{1 - .0806917\,V + .00243265\,V^2}$$

HC: $$\text{VOLTAGE} = \frac{-.00101937 + .00604898\,(\text{CON})}{1 + .000099042\,(\text{CON}) + .00000000291569\,(\text{CON}^2)}$$

CO: $$\text{VOLTAGE} = \frac{.234341 + 4.286\,(\text{CON}) + .639414\,(\text{CON}^2)}{1 + .760362\,(\text{CON}) + .0212465\,(\text{CON}^2)}$$

CO$_2$: $$\text{VOLTAGE} = \frac{.0685556 + 1.09018\,(\text{CON})}{1 + .0731536\,(\text{CON}) - .000700837\,(\text{CON}^2)}$$

METHOD AND APPARATUS FOR EMISSION TESTING

CROSS REFERENCE TO RELATED APPLICATIONS

This application is related to application Ser. No. 148,974, filed Jan. 27, 1988, entitled Dual Ported Speed Up Memory, application Ser. No. 148,973 filed Jan. 27, 1988, entitled Flag Generation System, and application Ser. No. 148,972, filed Jan. 27, 1988, entitled Flag Identification System, all of which are assigned to Sun Electric Corporation and all of which are hereby incorporated by reference.

BACKGROUND OF THE INVENTION AND PRIOR ART

This invention relates generally to automotive emissions testers and particularly to automotive emissions testers that are used with or in computerized engine testing equipment such as that described in the above mentioned related patent applications. The recently introduced Modular Computer Analyzer, known as the Sun MCA 3000, utilizes an IBM compatible computer in conjunction with a data acquisition system (DAS) that incorporates flagged data and an analog to digital (A/D) RAM that is accessible by both the DAS controller and a system microprocessor. A feature of the MCA 3000 is its ability to perform automotive emissions testing in a simpler, faster and more reliable manner.

A so-called emissions test bench uses infrared light and appropriate optical filters to develop an analog voltage that is indicative of the concentrations of particular gases. The particular gases are hydrocarbons (HC), carbon monoxide (CO), and carbon dioxide (CO2). An oxygen (O2) concentration measurement may also be obtained, but the apparatus therefor is not part of the present invention.

Automotive emissions testing, while generating extreme interest recently, is not new. The particular emissions test bench used with the present invention has also been in use for some time and is not part of the invention.

With prior art emissions test bench assemblies, a large number of potentiometers were required for factory and field calibration. It was also advisable to periodically recalibrate testers with a sample gas (cal gas) of known concentration. The cal gas is actually a mixture of Hexane (chemical formula C6H14), CO, and CO2 which provides the different hydrocarbons included in the tests. Recalibration required adjustments of the various potentiometers.

The emissions test bench is essentially a spectral photometric gas analyzer that uses a beam of infrared light to determine concentrations of various gases. The gases absorb different amounts of light at different wavelengths and the amount of light absorbed at a specific wavelength is related to the concentration, i.e. the number of molecules of the specific gas. The bench includes optical filters and sensors. The voltage output of the test bench is non-linear and the number of molecules in a sample cell of gas will change depending upon the pressure in the sample cell.

The prior art IR test bench assembly is equipped with amplifiers to increase its voltage output or span. The normal voltage span for such a bench assembly is from 0 to 10 volts. In the MCA 3000 automotive computer analyzer, the DAS converter has a range of from $-10$ to $+10$ volts. In accordance with one aspect of the invention, the emissions test bench assembly output voltage is offset to substantially center it within the range of the A/D converter. According to another aspect of the invention, any gain factor that is present in the bench assembly is measured. Information concerning the calibration pressure, the offset voltage and the gain factor is stored in non-volatile memory and is made accessible to the system microprocessor. These data are thus available to the computer and are used, in accordance with the invention, to self-compensate the test bench assembly output for any difference in pressure between the sample gas and the calibration pressure and to automatically compensate for the zero offset of the test bench assembly and any gain factor each time the bench is recalibrated. By utilization of all aspects of the invention, the emissions test bench assembly rarely, if ever needs to be recalibrated in the field. Also as will be seen, the type of calibration required in the field is simple, automatic for the most part and undemanding on the part of the user.

OBJECTS OF THE INVENTION

A principal object of the invention is to provide a novel emissions analyzer.

Another object of the invention is to provide an emissions analyzer that does not require periodic calibration.

A further object of the invention is to provide an emissions analyzer that is self compensating for pressure changes.

BRIEF DESCRIPTION OF THE PARTS

These and other objects of the advantages of the invention will be apparent upon reading the following description in conjunction with the drawings in which:

FIG. 3 is a series of equations used to correlate voltage and gas concentration.

DESCRIPTION OF THE PREFERRED EMBODIMENT

Figure 1:
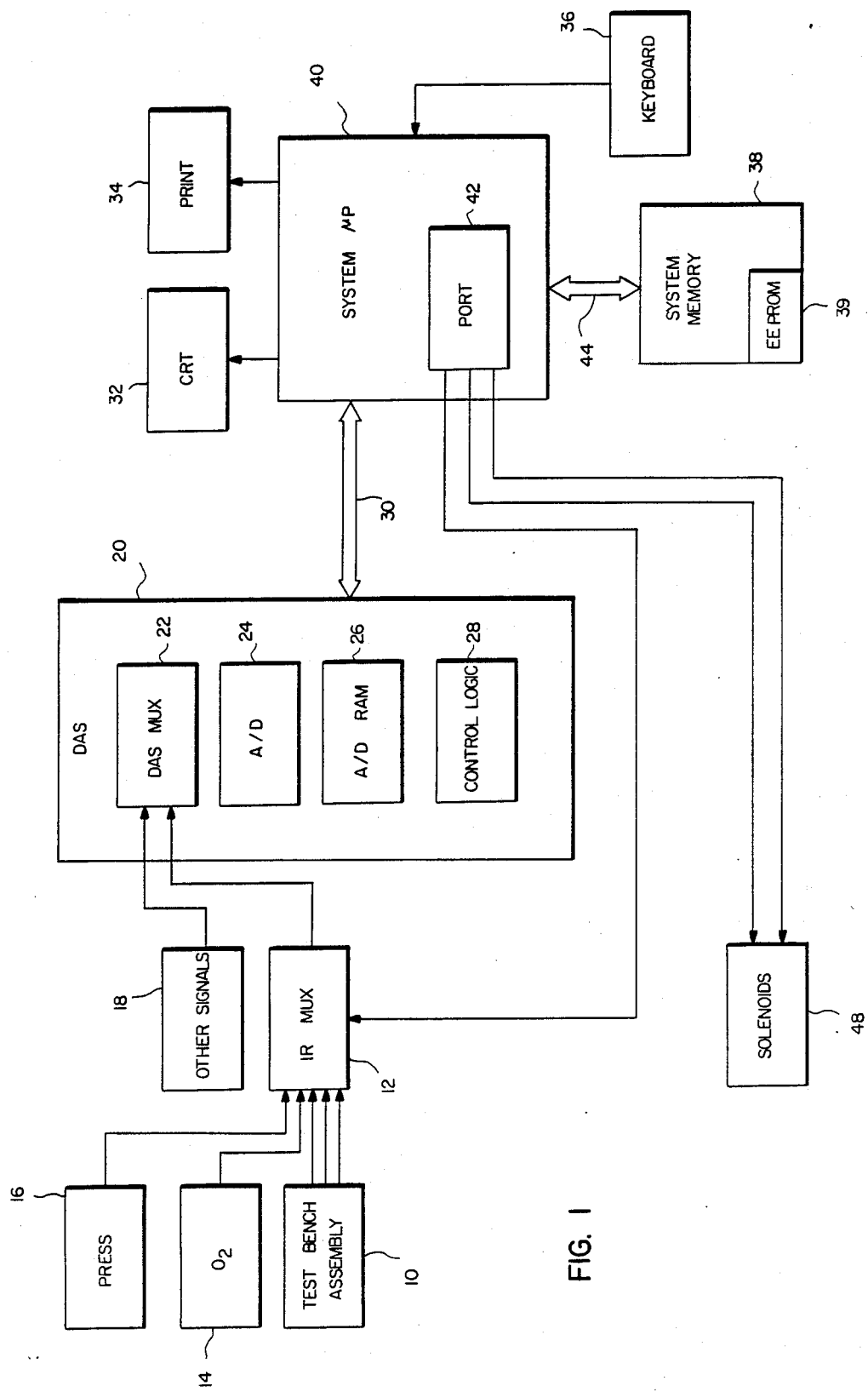
FIG. 1 is a partial block diagram of a computer analyzer constructed in accordance with the invention.

Referring to FIG. 1, a test bench 10 assembly provides a plurality of output voltages to an IR multiplexer (MUX) 12. An oxygen sensor 14 and a pressure sensor 16 also supply signals to MUX 12. The single output of MUX 12 is coupled to a DAS 20 which includes a DAS multiplexer 22, an A/D converter 24, an A/D RAM 26 and control logic 28. As is described in the above mentioned copending applications, DAS 20 operates independently to accept analog signals from MUX 12, or other engine test signals from a source 18, and supply them to A/D converter 24. After conversion to digital form they are loaded into A/D RAM memory 26 under control of control logic 28. A bidirectional communications bus 30 interconnects DAS 20 with a system microprocessor 40. A CRT display 32 and a printer 34 are operable under control of microprocessor 40 which as mentioned is preferably IBM compatible. A keyboard 36 is used to input user commands. A bidirectional communication bus 44 couples microprocessor 40 to a system memory 38 which includes a Section 39 of EEPROM. Microprocessor 40 also includes an output port 42 that is coupled by a group of control lines 46 to a plurality of solenoids 48 for controlling flow of the various gases and the like. Another group of control lines 50 connects port 42 to MUX 12. The operation of MUX 12 is under control of system microprocessor 40.

Figure 2:
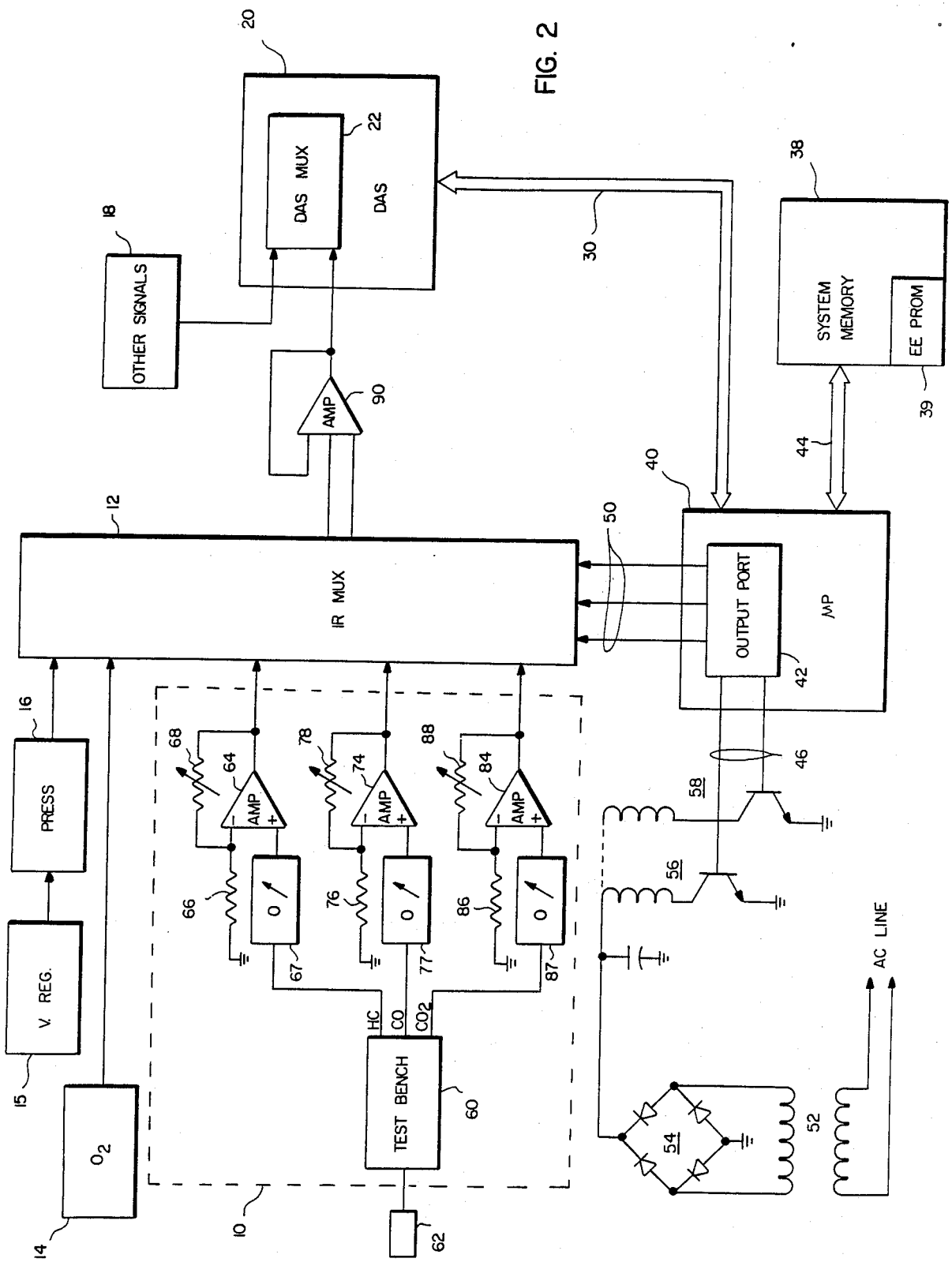
FIG. 2 is a partial schematic diagram of the emissions testing portion of FIG. 1.

FIG. 2 shows circuit details of test bench assembly 10, shown in dashed lines. A power transformer 52 is coupled to an AC line and to a DC rectifier arrangement 54 for developing appropriate DC voltages for application to transistor operated solenoids 56 and 58, that are controlled via control lines 46 from output port 42 of microprocessor 40. It will be appreciated that the various valves controlled by the solenoids are not shown and that the dotted line connecting transistor operated solenoids 56 and 58 indicates that a larger number may be used.

An emissions test bench 60 is supplied with emissions for analysis by means of a test probe 62 that gathers the automotive exhaust emissions. The three output leads from test bench 60, labelled HC, CO and CO2, carry analog voltages representative of the concentrations of HC, CO and CO2 gases in the emission sample. The voltages are applied to the non-inverting terminals of operational amplifiers 64, 74 and 84 through zero adjusting circuits 67, 77 and 87 respectively to set the zero output voltages of test bench 60 to correspond to a zero concentration of the respected gases in the emissions sample. The inverting terminals of these operational amplifiers are connected to ground through resistors 66, 76, and 86 respectively. Three feedback potentiometers 68, 78, and 88 are connected from the outputs to the inverting terminals of operational amplifiers 64, 74, and 84 respectively, and in conjunction with resistors 66, 76 and 86 provide gain adjustments for adjusting the voltage outputs (spans) therefrom. The outputs of the operational amplifiers are also supplied to IR MUX 12. Signals on the control leads 50 to MUX 12 are effective to select which of the input voltages appear in the output of the MUX 12, and is therefore supplied to a buffer amplifier 90. The output of buffer amplifier 90 feeds the selected voltage to DAS multiplexer 22 in DAS 20.

As mentioned, the voltage range of the A/D converter 24 (FIG. 1) is greater than the output voltage range or span from test bench 60. Experience indicates that the test bench zero point is much more likely to drift with temperature change and component tolerances than its span. By using an A/D converter with a larger range than the span of the test bench, the zero voltage of the test bench may be offset to substantially center it within the range of the A/D converter. This permits the test bench to drift a significant amount and still stay within the range of the A/D converter. Consequently the need for periodic calibration of the tester is obviated and whatever calibration may be required may be accomplished automatically.

As mentioned, a sample cell is used in conjunction with the IR test bench to analyze and determine the concentrations of the various gases in exhaust emissions. The sample cell provides a fixed volume and the IR test bench actually measures the number of molecules of the gas in the sample cell. Pressure changes will affect the number of molecules and the readings, and by measuring the pressure in the sample cell during the exhaust emissions test the errors due to pressure changes can be corrected. The equation for determining the number of molecules in the sample cell at the time of calibration of the tester is:

$$\frac{P}{N} = \frac{KT}{V}$$

where P is the pressure, N is the number of molecules, T is the temperature, V is the volume of the sample cell and K is a constant. It is readily seen that if the temperature and volume remain constant a change in pressure will result in a change in the number of molecules. Thus by measuring the pressure at the time of calibration and storing that measurement, later test measurements at different pressures can be corrected for the error due to pressure change. The equation for this is:

$$N\text{corr} = \frac{P\text{cal}}{P\text{meas}} \times N\text{meas}$$

Normally a lookup table is supplied by the IR bench manufacturer for converting the measured voltage to a gas concentration and vice versa. Interpolation between the nearest two points is usually required with the look up table.

Reference to FIG. 3 shows six polynomial equations that have been derived which relate concentration to voltage, and voltage to concentration, for the different gases HC, CO and CO2. With these polynomial equations, lookup tables are obviated and the computer may perform all calculations.

To calibrate the test bench, a zero reading and a span reading are taken with a known calibration gas (cal gas). The zero value for each measured gas (HC, CO and CO2), is stored in non-volatile memory. The non-volatile memory may be a conventional memory with a back up battery or it may be a memory of the EEPROM type. By using the lookup tables or the equations, the voltage that should be developed by the test bench can be readily determined. The span reading measured during calibration is divided by the span reading found from the tables and the gain factor of the test bench is computed. It will be appreciated that a desired span or voltage may be used rather than that found from the tables in order to provide more resolution in the test bench voltage. The gain factor for each measured gas is stored in non-volatile memory. The calibration pressure is measured and stored in non-volatile memory. When the unit is now turned on and warmed up new zero values are taken and stored in RAM memory. By taking the zero reading, any long term drift of the IR test bench zero is corrected for.

To display a gas concentration, the analog voltage from the test bench is first corrected for the zero offset. This is performed by subtracting the zero reading taken after the unit is warmed up. Then the voltage is corrected for the gain factor of the test bench. This is accomplished by dividing by the gain factor that was computed during calibration and stored in the non-volatile memory. Then the voltage is corrected for any pressure difference from the pressure measured at calibration. This is accomplished by multiplying the voltage by the ratio of the pressure at calibration and the pressure measured in the sample cell. The equation for this is:

$$V\text{corr} = \frac{V\text{meas} - V\text{zero}}{\text{Gain}} \times \frac{P\text{cal}}{P\text{meas}}$$

This voltage can now be converted to a gas concentration through use of the lookup tables or use of the polynomial equations.

The oxygen sensor is not part of the present invention. Suffice it to say that the oxygen sensor has a linear output and consequently does not require a lookup table or polynomial equation. Because of the differences in each oxygen sensor, these readings cannot be compensated for pressure changes.

It should be apparent to those skilled in the art that with the invention, the need for a large number of potentiometers (generally coarse and fine potentiometers) is eliminated. Also the setting of potentiometers is not critical thus relieving factory personnel (and field personnel) of the need for precise adjustments to calibrate the bench. Should calibration in the field be needed or desired, the user may readily calibrate the unit without needing to adjust the potentiometers.

It is recognized that numerous modifications and changes in the described embodiment of the invention will be apparent to those skilled in the art without departing from its true spirit and scope. The invention is to be limited only as defined in the claims.

What is claimed is:

1. An emissions tester comprising:
    means for calibrating said tester with a test sample having a known concentration of a particular gas;
    means for storing pressure data for said test sample in a non volatile memory;
    means for developing an analog voltage signal representative of the concentration of said particular gas in an exhaust emission;
    an analog to digital converter for converting said analog voltage signal into a digital value, the range of said analog to digital converter being greater than the span of said analog voltage;
    means for offsetting said analog voltage to substantially center it within the range of said analog to digital converter;
    means for storing data, related to the amount of voltage offset, in a non-volatile memory;
    means for correcting said analog voltage signal by said stored offset data;
    means for sensing the pressure of said exhaust emission;
    means for compensating said analog voltage signal based upon the difference in the sensed pressure and the stored pressure;
    means for storing a gain factor in a non-volatile memory for relating said calibration voltage to a desired voltage; and
    means for adjusting said analog voltage signal by said stored gain factor.

2. The emission tester of claim 1 wherein said non-volatile memories are EEPROMs.

* * * * *